United States Patent
Chaudhury et al.

(10) Patent No.: US 12,311,067 B2
(45) Date of Patent: May 27, 2025

(54) LIQUID, AIR, AND SURFACE TREATMENT USING HIGH INTENSITY BROAD-SPECTRUM PULSED LIGHT AND METHOD USING THE SAME

(71) Applicant: Aruna Inovation LLC, Bayonne, NJ (US)

(72) Inventors: Ameet Chaudhury, Bayonne, NJ (US); Shekhar Chandrashekhar, Trabuco Canyon, CA (US); Sameer Neve, Jersey City, NJ (US)

(73) Assignee: ARUNA INOVATION LLC, Bayonne, NJ (US)

( * ) Notice: Subject to any disclaimer, the term of this patent is extended or adjusted under 35 U.S.C. 154(b) by 938 days.

(21) Appl. No.: 17/464,994

(22) Filed: Sep. 2, 2021

(65) Prior Publication Data

US 2023/0061524 A1 Mar. 2, 2023

(51) Int. Cl.
*H05B 41/14* (2006.01)
*A61L 2/10* (2006.01)
(Continued)

(52) U.S. Cl.
CPC ....... *A61L 2/10* (2013.01); *A61L 2/26* (2013.01); *B08B 7/0057* (2013.01); *H05B 41/14* (2013.01); *H05B 41/30* (2013.01); *H05B 41/36* (2013.01)

(58) Field of Classification Search
CPC ........ H05B 41/14; H05B 41/24; H05B 41/30; H05B 41/34; H05B 41/36; H05B 41/288;
(Continued)

(56) References Cited

U.S. PATENT DOCUMENTS 4,839,686 A * 6/1989 Hosomizu ............... G03B 15/05
  396/156
5,249,007 A * 9/1993 Tanaka ................... H05B 41/32
  315/241 P
(Continued)

FOREIGN PATENT DOCUMENTS

CN 111885763 A 11/2020
WO 2016168139 10/2016

OTHER PUBLICATIONS

International Search Report and Written Opinion of PCT/US2022/075842, Dec. 27, 2022, 11 pages.
(Continued)

*Primary Examiner* — Tung X Le
(74) *Attorney, Agent, or Firm* — HSML P.C.

(57) ABSTRACT

An adjustable power supply circuit for a treatment and/or disinfection system using high intensity broad-spectrum pulsed light that includes a capacitor power supply, a capacitor bank connected to the capacitor power supply and a high intensity light source, a trigger circuit including a trigger coil connected to the high intensity light source, and a controller. The capacitor bank includes a plurality of capacitors connected in series and/or in parallel, where the capacitor bank is adjustable to adjust an amount of energy supplied to the high intensity light source. The controller receives input data and controls charging of the capacitor bank by the at least one capacitor power supply to power the high intensity light source at a desired voltage and triggers the trigger circuit to turn on the light source at the desired voltage to strobe pulsed light with an amount of fluence to treat contaminants.

16 Claims, 5 Drawing Sheets

(51) Int. Cl.
 *A61L 2/26* (2006.01)
 *B08B 7/00* (2006.01)
 *H05B 41/30* (2006.01)
 *H05B 41/36* (2006.01)

(58) Field of Classification Search
 CPC ............ H05B 41/2806; H05B 41/2824; H05B 41/2828
 See application file for complete search history.

(56) References Cited

U.S. PATENT DOCUMENTS

| | | | | |
|---|---|---|---|---|
| 5,654,611 | A * | 8/1997 | Yamamoto | H05B 41/2882 |
| | | | | 315/308 |
| 6,661,184 | B2 * | 12/2003 | Okamoto | H05B 41/2881 |
| | | | | 315/261 |
| 7,218,205 | B2 * | 5/2007 | Fisler | G08B 5/38 |
| | | | | 396/206 |
| 7,675,244 | B2 * | 3/2010 | Blondia | H05B 41/2928 |
| | | | | 315/307 |
| 7,859,229 | B2 * | 12/2010 | Hoshikawa | G03B 15/05 |
| | | | | 307/110 |
| 9,889,217 | B2 | 2/2018 | Franc et al. | |
| 10,485,887 | B2 | 11/2019 | Ramanand et al. | |
| 2004/0034398 | A1 | 2/2004 | Eckhardt et al. | |
| 2004/0251851 | A1 * | 12/2004 | Maishima | H05B 41/32 |
| | | | | 315/291 |
| 2006/0074468 | A1 | 4/2006 | Neev | |
| 2007/0247080 | A1 | 10/2007 | Tipton | |
| 2020/0085983 | A1 | 3/2020 | Ramanand et al. | |
| 2020/0161069 | A1 | 5/2020 | Ramanand et al. | |

OTHER PUBLICATIONS

"Pulsed Light Sterilization of Packaging Equipment Manufacturer—Our Pulsed light Sterilization Solutions" Clananor, https://www.claranor.com/en/; accessed on Sep. 1, 2021; 4 pages.

"LightStrike_Robot—Destroy Deadly Pathogens to Improve Peace of Mind" Xenex, https://xenex.com/; accessed on Sep. 1, 2021; 10 pages.

"Pulsed UV robotics. For a New Era of Clean." Solaris https://solarisrobots.com/; accessed on Sep. 1, 2021; 6 pages.

* cited by examiner

LIQUID, AIR, AND SURFACE TREATMENT USING HIGH INTENSITY BROAD-SPECTRUM PULSED LIGHT AND METHOD USING THE SAME

FIELD OF THE DISCLOSURE

The present disclosure is generally related to treating, purifying, disinfecting, or sterilizing liquid, air, food and crop, or surfaces using high intensity broad-spectrum pulsed light, high intensity pulsed light (HIPL), high intensity broad-spectrum pulsed light (BSPL), or pulsed white light (PWL) at a predetermined or tunable pulse rate, frequency, fluence (radiant exposure), peak power, exposure time, and/or pulse width to eliminate, reduce, degrade, or render inert or nullify physical, chemical or microbiological contaminants that includes a non-mercury flash lamp. The present disclosure is also related to a smart system that may function an as IoT (internet of things) device. IoT is a system of interrelated computing devices, mechanical and digital machines provided with unique identifiers and the ability to transfer data over a network without requiring human-to-human or human-to-computer interaction.

BACKGROUND

Liquid and surface treatment are processes that are used for disinfection of liquids, air, food and crops, and high-contact surfaces. Liquid treatment removes contaminants and other undesirable components, or reduces the concentration of those contaminants and undesirable components or renders such undesirable or harmful components inert so that the liquid becomes fit for the intended use. Surface treatment disinfects a surface, such as a table, countertop, surgical bed, door, desk, etc., or food and crop surfaces from physical, chemical, biological and microbiological contaminants, for example, by deactivating harmful germs.

The destruction of physical, chemical, biological and microbiological contaminants very commonly involves the use of reactive chemical agents. However, residual chemical agents in such treated liquid or high-contact surface may cause illness or even death. In traditional light based liquid treatment and surface treatment systems, the high consumption of energy and high floor space requirement have proven to be less efficient.

A non-chemical, non-mercury, scalable liquid and surface treatment systems and methods with low cost and reliable liquid and surface disinfection is desired. Traditional light based sterilization methods are typically large in size and expensive and reserved for very specific use cases.

SUMMARY

In at least one example embodiment, a scalable liquid, air, or surface treatment system using pulsed light to eliminate, reduce, degrade, or render inert or nullify physical, chemical, or microbiological contaminants includes a power supply circuit for supplying power to a high intensity broad-spectrum pulsed light source. The power supply circuit includes at least one capacitor power supply to supply power to a capacitor bank. The capacitor bank is connected to the at least one capacitor power supply and a high intensity light source, where the capacitor bank includes a plurality of capacitors connected in series and/or in parallel, where the capacitor bank is configured to be adjustable to adjust an amount of energy supplied to the high intensity light source. The power supply circuit also includes a trigger circuit including a trigger coil connected to the high intensity light source for triggering on the high intensity light source and a controller. The controller is configured to receive input data from at least one of a sensor or data source, control charging of the capacitor bank to power the high intensity light source at a desired voltage by controlling voltage from the at least one capacitor power supply, and trigger the trigger circuit to turn on the high intensity light source at the desired voltage, where the desired voltage is based on at least the input data to determine an amount of fluence necessary to treat contaminants using strobe pulsed light.

In at least one example embodiment, the capacitor bank includes at least two capacitor banks connected in parallel, where the controlled charging of the at least two capacitor banks includes charging at least one of the at least two capacitors banks at a low voltage and/or charging the other of the at least two capacitors banks at a high voltage.

In at least one example embodiment, the controller is further configured to stop the at least one power supply from charging the capacitor bank when the trigger circuit is trigged to turn on the high intensity light source.

In at least one example embodiment, the high intensity light source includes a non-mercury flash lamp to generate the pulsed light.

In at least one example embodiment, the plurality of capacitors are pulse-type capacitors that are connected in series and parallel to supply a specific amount of energy to the high intensity light source.

In at least one example embodiment, the high intensity light source is a xenon lamp.

In at least one example embodiment, the power supply circuit further includes an insulated-gate bipolar transistor connected to the high intensity light source, where the insulated-gate bipolar transistor provides a current path for the voltage supplied to the high intensity light source.

In at least one example embodiment, the power supply circuit further includes at least one of a solid state storage module, a cellular module, a Wi-Fi module, and a Bluetooth module, where at least one of the solid state storage module, the cellular module, the Wi-Fi module and the Bluetooth module is configured to receive input data from the at least one sensor or data source.

In at least one example embodiment, the trigger circuit includes a trigger power supply, first resistor, a first capacitor, a silicon controlled rectifier, and a trigger coil, where the first resistor, the first capacitor, the silicon controlled rectifier, and the trigger coil are configured to produce a high voltage pulse to trigger the high intensity light source on.

In at least one other example embodiment, a method of using pulsed light to eliminate, reduce, degrade, or render inert or nullify physical, chemical or microbiological contaminants in a liquid flow includes receiving input data from at least one of a sensor or data source, determining a voltage for an amount of fluence necessary for the treatment of any contaminants, and charging a capacitor bank from at least one capacitor power supply, where the charging the capacitor bank includes charging the capacitor bank to the voltage. The capacitor bank is connected to the at least one capacitor power supply and a high intensity light source, where the capacitor bank includes a plurality of capacitors connected in series and/or in parallel, where the capacitor bank is configured to be adjustable to adjust an amount of energy supplied to the high intensity light source. The method further includes triggering a trigger circuit having a trigger coil connected to the high intensity light source to turn on the high intensity light source, and controlling the high intensity light source at the voltage to strobe pulsed light with the necessary fluence to treat the contaminants.

It is appreciated that the above embodiments are merely illustrative of the technical concept and features of liquid, air, or surface treatment with pulsed light, and these embodiments are to make a person skilled in the art understand the contents of the treatment system and to implement the treatment system without limiting the scope of protection of the treatment system. Any features described in one embodiment may be combined with or incorporated/used into the other embodiment, and vice versa. The equivalent change or modification according to the substance of the treatment system should be covered by the scope of protection of the treatment system.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

The present disclosure provides a detailed and specific description that refers to the accompanying drawings. The drawings and specific descriptions of the drawings, as well as any specific or alternative embodiments discussed, are intended to be read in conjunction with the entirety of this disclosure. The liquid, air, or surface treatment system may, however, be embodied in many different forms and should not be construed as being limited to the embodiments set forth herein; rather, these embodiments are provided by way of illustration only and so that this disclosure will be thorough, complete and fully convey understanding to those skilled in the art.

References are made to the accompanying drawings that form a part of this disclosure and which illustrate embodiments in which the systems and methods described in this specification may be practiced.

DETAILED DESCRIPTION

Some embodiments of this disclosure, illustrating all its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a", "an" and "the" include plural references unless the context clearly dictates otherwise. Although any systems and methods similar or equivalent to those described herein may be used in the practice or testing of embodiments of the present disclosure, the preferred systems and the preferred methods are now described.

It is appreciated that embodiments disclosed herein use high intensity broad-spectrum pulsed light, high intensity pulsed light (HIPL), high intensity broad-spectrum pulsed light (BSPL), or pulsed white light (PWL), etc., and these types of light hereinafter are referred to as "light" or "pulsed light". A broad use case (e.g., liquid, air, and surface sterilization method) with affordability is desired for, e.g., to sterilize high contact surfaces from viruses, bacteria and other harmful substances, for example, during pandemic times. The high intensity pulsed light can be, for example, gas-discharge arc lamps that create the broad-spectrum light when an electrical discharge is sent between two electrodes through the ionized gas. It is appreciated in some embodiments, the high intensity broad-spectrum pulsed light is from a non-mercury flash lamp.

Embodiments of the present disclosure are described more fully hereafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

Figure 1A:
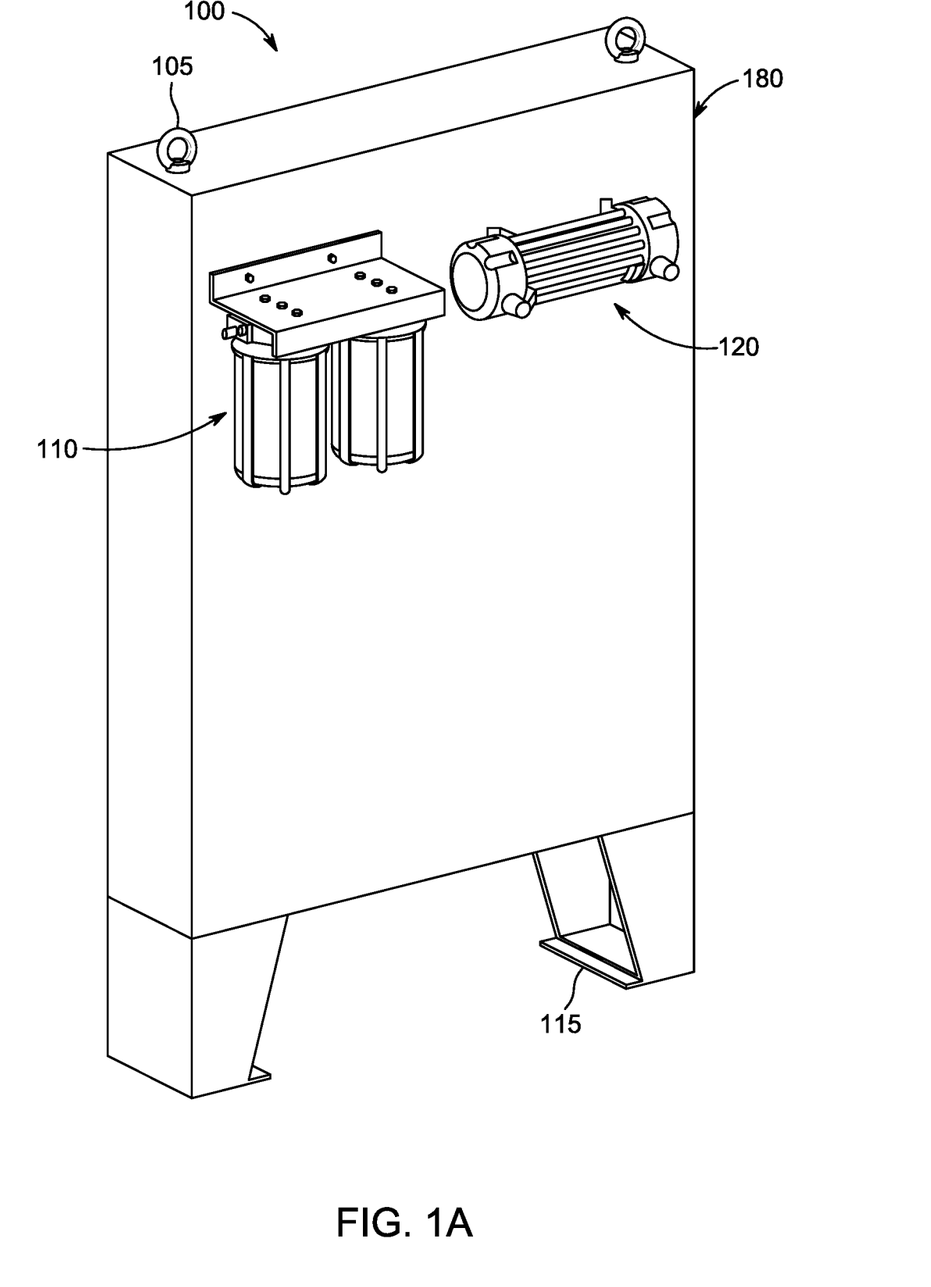
FIGS. 1A-1B are structural schematic diagrams of a liquid treatment system viewed at different angles, according to at least one example embodiment described herein.
Figure 1B:
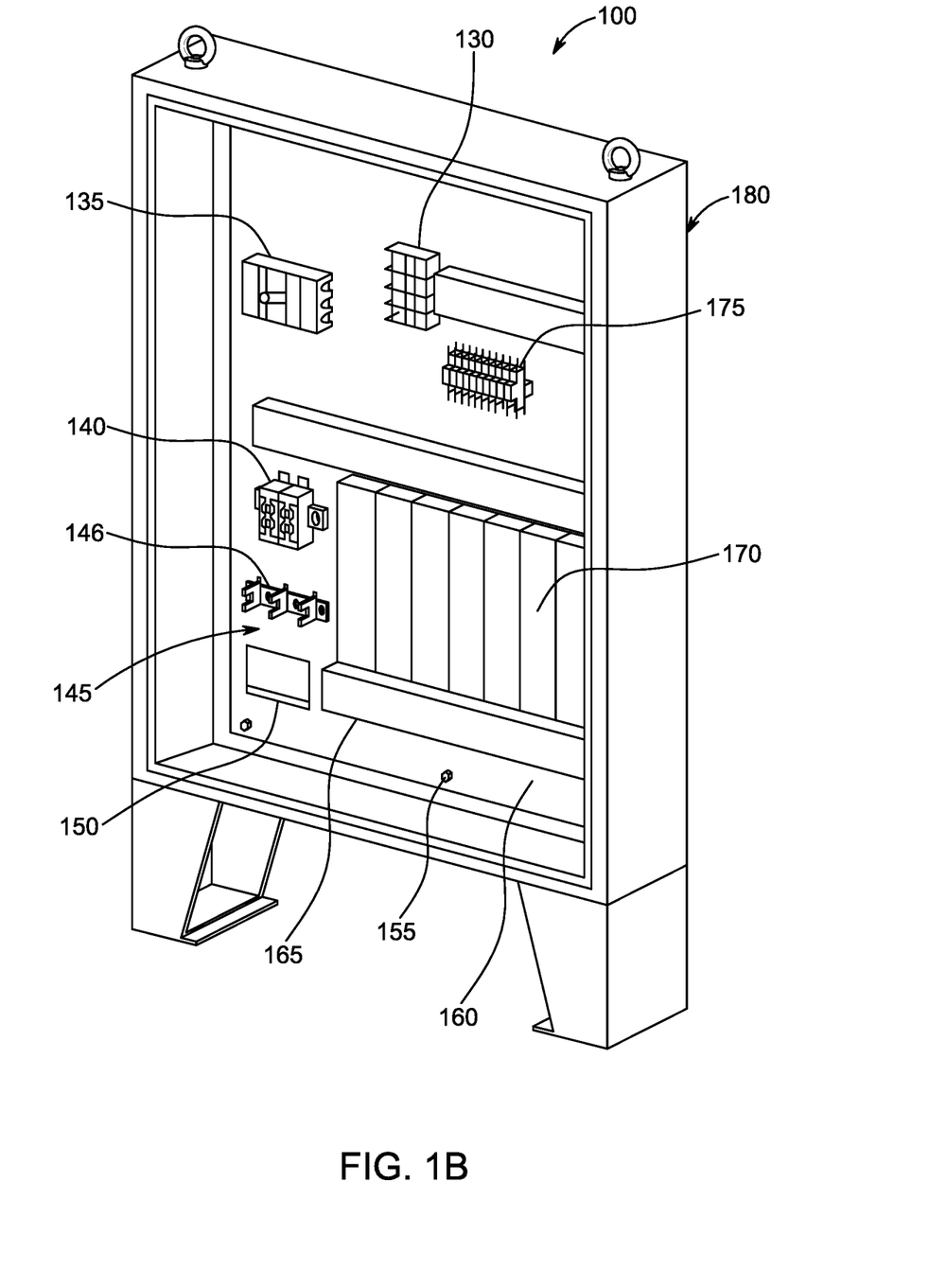

FIGS. 1A-1B are structural schematic diagrams of one embodiment related to a liquid treatment system 100 viewed at a front side and back side. Such a liquid treatment system 100 is known, for example, as disclosed in U.S. application Ser. No. 16/899,128 filed Jun. 11, 2020, which is incorporated herein by reference.

The system 100 includes a housing 180, e.g., a sterilization housing or cabinet that houses electrical components of the system 100 and provides a mounting plane for the sterilization components (110, 120) of the system 100 on the reverse/back side of the housing 180. Example embodiments of the system 100 may be installed at a liquid filtration facility, at homes, in buildings, on ships, or next to a liquid source such as a stream, a river, or a lake, as non-limiting example environments. It is appreciated that the system 100 overall may cover all aspects of a smart system that could function an as IoT (internet of things) device, where the various components can include Bluetooth, Wi-Fi, or cellular capabilities.

FIG. 1A shows a rear/back side of the housing 180, which includes, at least, a filter sub-system 110. In at least one non-limiting example embodiment, the filter sub-system 110 is a dual filtration (including two filters) system that is capable of receiving and treating liquid. The system 100 may also include a reactor 120 that is connected to the filter sub-system 110. The liquid pipe(s) and the connection assemblies are not shown. In at least one example embodiment, the filter sub-system 110 is optional.

The reactor 120 sterilizes, disinfects and/or treats the liquid flow flowing through the reactor 120. In at least one example embodiment, the reactor 120 provides intense pulsed light to sterilize, disinfect and/or treat approximately 30 gallons of liquid per minute flowing through reactor 120. The embodiments herein are provided as examples only, and therefore other embodiments of reactor 120 are contemplated that are not limited to a volume of 30 gallons per minute.

FIG. 1B shows a front/front side of the system 100, which includes the electronic components therein. The system 100 includes a circuit breaker 135, power rails 130 to distribute electrical power, and outlets 140 that may include, e.g., Quad Din mounted outlets to provide individual duplex controlled outlets for internal control systems (e.g., at or about 120 volts system such as the control system 145) independent to the power supplied (e.g., 170) for the sterilization subsystem (110, 120). The circuit breaker 175 is a secondary shutoff system that allows a single component of the system 100 to fail without causing the entire system 100 to fail, and further allows individual components of the system 100 to be powered down. The control system has a power supply (and outlets 140) independent of the power supplied to the sterilization subsystem (110, 120) because the sterilization subsystem (110, 120) has specific power supply distribution specifications and outlets for strobing/flashing.

The system 100 also includes a control system 145. In at least one example embodiment, the control system 145 includes one or more processing boards having a controller 146/processor (e.g., an ARM processor) running control algorithm allowing individual digital multiplex (DMX) control of each of the components of the system 100 through, e.g., a control algorithm which may include for e.g., deep learning, machine learning and/or artificial intelligence systems. In an embodiment, the control algorithm can receive as input data, sensor data and/or data from a data base to determine the amount of fluence to be outputted by the reactor 120 for a disinfection rate of over 99%. The controller 146 allows the adjustable control of the system 100 by controlling the amount of fluence based on a number of factors, including but not limited to environmental data, ozone generation, sound generation, temperature of any of the system components, energy provided, and distance from the contaminated surface, liquid, or object.

The system 100 further includes an input/output device 150 that may be a touch-screen interface screen or display device such as a LED/LCD connected to the controller 146 of the ARM processing boards of the control system 145 to facilitate control (e.g., by a user) of the control system 145. It is appreciated that access/control to the controller 146 may be remote via, e.g., through a web browser, a mobile app, etc. For example, the controller 146 can include at least one of a Bluetooth module, Wi-Fi module, or cellular module for accessing/controlling the controller 146, where any of the Bluetooth module, Wi-Fi module, or cellular module can be used for communication with the sensor or data base for transmitting/receiving input/output data to facilitate the control of the system 100. The system 100 also includes a circuit breaker 175 that may be an Eaton miniature circuit breaker (current-limiting, 20 A, Din mountable unit, etc.).

In an embodiment, the controller 146 can also include a SSD module and can receive a temperature input from at least one of the power supply system 170, the reactor 120, or internal temperature sensor to monitor the associated system. If a temperature exceeds an allowable temperature value, the controller 146 can be configured to provide an alarm signal or shut down the affected system or wait until the temperature reaches an operable temperature value.

The system 100 further includes a power supply system 170 that may be an individual flash power system, e.g., at or around 20 ampere current, and may include a DMX input/output to control each high intensity light source, e.g., lamps of the reactor 120 by, e.g., the controller 146 of the control system 145 can control on a one-to-one, one-to-multiple or multiple-to-multiple basis. For example, the controller 146 may control the power supply system 170 to power one or more lamps to flash individually or together with varying duration, intensity, etc., based on measured data. In an embodiment, the measured data can include UV spectrum detection, energy output, or remaining energy in the capacitor bank.

In at least one example embodiment, the controller 146 controls the DMX of the power system 170, by e.g., executing a control software. The control can be manual (e.g., via a user command through the input/output device 150), predetermined (e.g., with preset values of the DMX control parameters), or dynamic (adjusted based on current conditions such as available input power, liquid flow rate, amount of contaminants, detected contaminants, etc.). The controller 146 controls the DMX to control or synchronize the power supplied to the lamp(s) of the reactor 120. The power/energy supplied to the lamp(s) of the reactor 120 is the amount of intensity (or irradiance, duration, energy density, or dose, etc.) to flash the lamp(s) in the reactor 120.

The components 130, 135, 140, 145, 150, 170, 175, and 250 of the system 100, described above, may be disposed in the interior of the housing 180. It is appreciated that the system can include at least two power supplies (e.g., one to power the control system 145 and one to power the reactor 120), electrical power lines, and control lines to connect those components listed above, including sub-system 110 and reactor 120, to provide power thereto and to provide control by the controller 146. The electrical power lines and the control lines are not shown.

Figure 2:
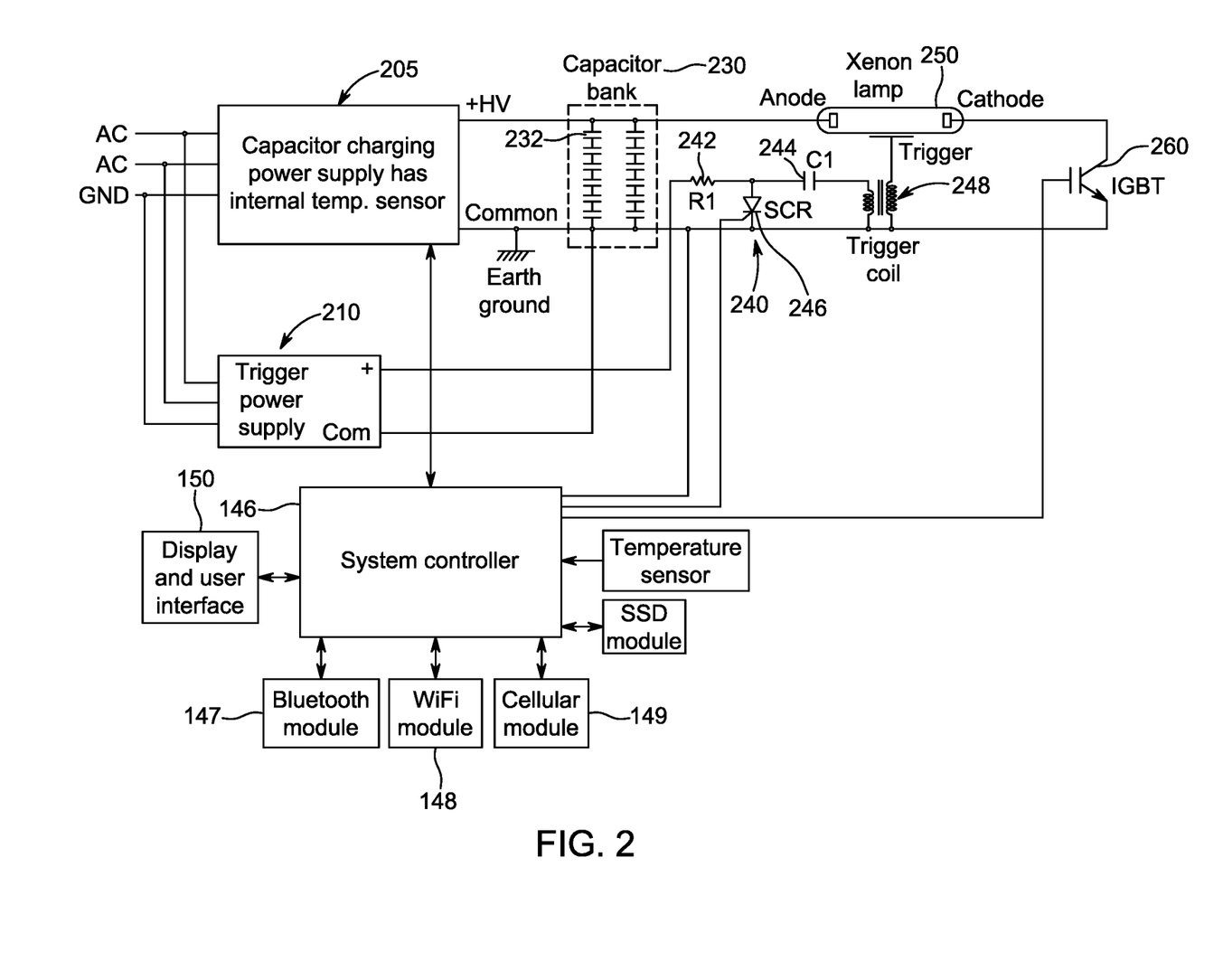
FIG. 2 is a schematic circuit diagram of a power supply, according to at least one example embodiment described herein.

FIG. 2 shows a schematic representation of one embodiment of the power supply 170 for supplying power to at least one high intensity light source. Specifically, the power supply 170 is used to charge a set of capacitor bank(s) to supply a predetermined voltage and power necessary for the high intensity light source(s), and to supply the power for triggering the flashing of the at least one high intensity light source. It is appreciated that multiple power supplies can be provided for each high intensity light source, e.g., one-to-one basis, or a single power supply can be used for multiple high intensity light sources, e.g., one-to-multiple basis, or combination thereof without departing from the scope of the disclosure. For example, it is appreciated that if a single power supply is used to supply energy for multiple high intensity light sources, the power supply would include a larger set of capacitor bank(s) that would be able provide the necessary voltage for operating the multiple high intensity light sources.

As seen in FIG. 2, the power supply 170 includes a capacitor charging power supply 205 and a trigger power supply 210 connected to an external AC power supply. In at least one embodiment, the external power supply (not shown) for the control system is shore power/utility power (e.g., 100-240 volts, etc.). The capacitor charging power supply 205 and the trigger power supply 210 convert the AC power to high voltage direct current, e.g., using step-up transformers, that is required to operate and flash the high intensity light source. It is appreciated that the capacitor charging power supply 205 and the trigger power supply 210 can also be powered by DC power, where a battery power source(s) is provided. For example, the capacitor charging power supply 205 and the trigger power supply 210 can include any of a combination of rectifier circuits, boost converters, step-up transformers, or similar voltage step-up circuits, or combinations thereof, to increase a DC power supply to the predetermined voltage necessary for the high intensity light source.

The capacitor charging power supply 205 is connected to a capacitor bank 230 via the high voltage output of the capacitor charging power supply 205, where the capacitor bank 230 comprises a plurality of capacitors 232. The capacitors 232 can be pulse type capacitors that are connected in series to increase the voltage rating of the capacitor bank 230 and/or in parallel to increase the capacitance of the capacitor bank 230. The pulse type capacitors have ratings between 1000 and 10,000 uF, and preferably have a rating between 1000 and 5000 uF.

The capacitor bank 230 is able to store an adjustable amount of electrical energy to supply to the high intensity light source as represented by the following equation:

$$E = \tfrac{1}{2} * C * V^2,$$

where E is the energy in Joules, C is the capacitance in Farads, and V is the voltage.

It is appreciated that while the voltage needed for the high intensity light source is dependent on the specific model of the high intensity light source, generally, the voltage necessary for operation of the high intensity light source ranges from about 200 volts to 3000 volts, and preferably from about 350 volts to 2000 volts, to have the high intensity light source emit between about 60 Joules to 3000 Joules per pulse, and preferably between 240 to 640 Joules per pulse, and most preferably over 600 Joules per pulse. It is appreciated that the voltage supply to the high intensity light source can be adjusted by adjusting the charge of the capacitors that are used in the capacitor bank as further discussed below.

Figures 3A, 3B:
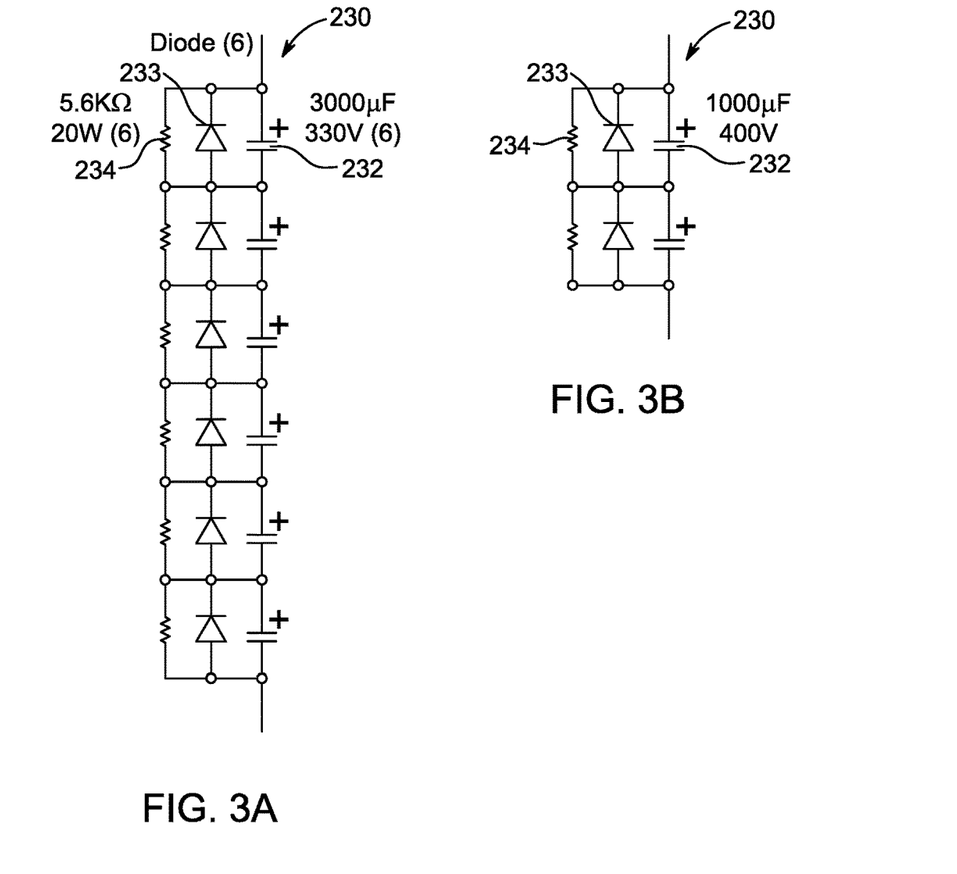
FIGS. 3A and 3B are schematic circuit diagrams of capacitor banks, according to at least one example embodiment.

FIG. 3A illustrates an embodiment of the invention that includes a high voltage capacitor bank, where the high voltage capacitor bank 230 includes at least six capacitors connected in series. Each of the capacitors 232 are electrically connected to a reverse biased diode 233, to protect the capacitors from reverse voltage during discharge, and a resistor 234 to assure that the capacitors all charge to the same voltage. Other means of assuring that the capacitors are charged to the voltage may be employed, such as using transistors, which could reduce the power losses of the resistors. In this embodiment, the capacitors 232 are pulse type capacitors having between a 3000 and 5000 uF and 250-450 V rating, and preferably a 3000 uF and 330 V rating. The six capacitors 232 connected in series can be used to supply a voltage that is adjustable from about 800 to 1600 V, where the capacitors are charged equally in series, and then discharged to supply the voltage needed to power the high intensity light source to provide the amount of fluence required for disinfection.

FIG. 3B illustrates an alternate embodiment or an embodiment that can be used in combination with the high voltage capacitor bank of FIG. 3A, that includes a low voltage capacitor bank 230. The low voltage capacitor bank 230 includes at least two capacitors 232 connected in series, where each of the capacitors 232 are electrically connected to a reverse biased diode 233 and a resistor 234. In this embodiment, the capacitors 232 are pulse type capacitors having a 1000 uF and 400 V rating. The two capacitors 232 connected in series can be used to supply a voltage that is adjustable from about 350 to 700 V, where the cell(s) are equally charged to supply the voltage needed to power the high intensity light source.

Figure 4:
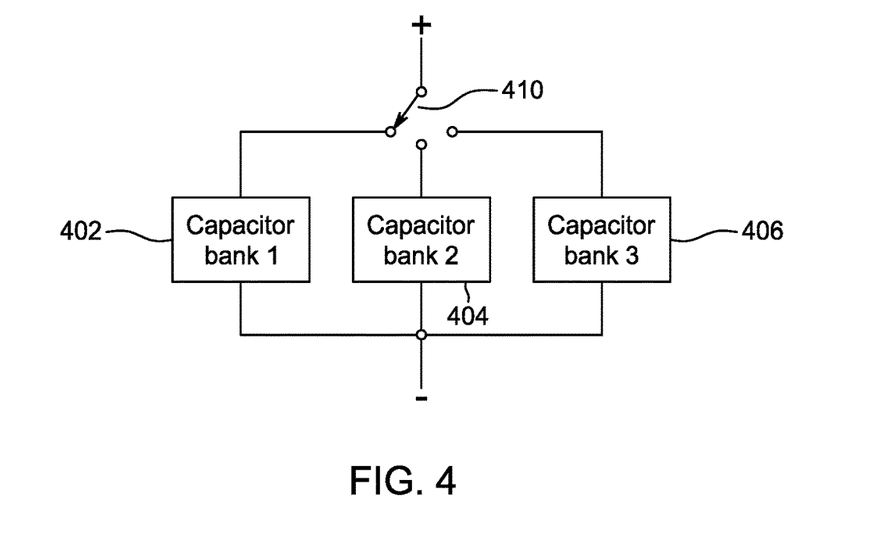
FIG. 4 is a schematic circuit diagram of a switch for multiple capacitor banks, according to at least one example embodiment.

As shown in FIG. 4, the high voltage capacitor bank 402 can be connected in parallel with the low voltage capacitor bank 404, and optionally a third capacitor bank 406, to supply varying amounts of energy to the high intensity light source. A switch 410 can be provided that electrically connects to one of the high voltage capacitor bank 402 and the low voltage capacitor bank 404, and optionally the third capacitor bank 406, to allow selectable and adjustable charging and discharging of the capacitor bank 230. The switching relay can be controlled manually or by the controller 146 based on the needs of the system and/or the high intensity light source and the amount of fluence necessary for disinfection. For example, when the switch is electrically connected to the high voltage capacitor back 402, the controller 146 can control the capacitor charging power supply 250 to supply a voltage between 800 and 1600 to the high voltage capacitor bank 402, when higher voltage is needed for the high intensity light source. Similarly, if a supply voltage between 350 and 700 is needed, the switch is electrically connected to the low voltage capacitor bank 404, and the controller 146 controls the capacitor power supply 250 to supply the lower voltage amount. It is appreciated that multiple switches can be provided that allow the charging and/or discharging of multiple capacitor banks. For example, the third capacitor bank 406 can also be a high voltage capacitor bank and can be charged during the discharging of the high voltage capacitor bank 402.

Turning back to FIG. 2, FIG. 2 shows that the capacitor bank 230 is connected to the anode of a high intensity light source 250, for example, a high intensity xenon lamp that is part of the reactor 120. The cathode of the high intensity light source 250 is connected to an insulated-gate bipolar transistor (IGBT) 260, where the IGBT 260 is connected to the controller 146. The IGBT 260 allows the lamp flash time to be shortened, thereby reducing the lamp energy, by having the system controller gate "OFF" the IGBT 260 during the flash, since it is connected in series with the high intensity light source 250, e.g., to allow adjustable flash durations by providing a current path for the voltage supplied to the high intensity light source. An IGBT used for this purpose can produce pulses ranging from 100 microseconds to over 20 milliseconds. An energy sensor, e.g., a pyroelectric or photodiode sensor, can also be provided to sense an energy of the pulsed light from the high intensity light source 250. Thus, the IBGT 260 with the system controller 146 can be used to adjust the energy supplied to the high intensity light source 250 at different pulse rates, e.g., ranging from 0.5 to 2 pulses per second, and cutting off the pulses over various pulse rates, e.g., termination after between 0.1-3 ms, and preferably at 0.5 ms, and energy level as necessary for the treatment and disinfection of the contaminants. It is appreciated that by shorting the lamp flash time, the voltage charged to the capacitor bank 230 may not be fully depleted and such energy can be used for various purposes, including providing the voltage necessary for another high intensity light source or for subsequent flashes of the high intensity light source 250.

The power supply 170 also includes a trigger power supply 210 connected to a trigger circuit 240 and the capacitor bank 230. The trigger circuit 240 includes a resistor 242, a capacitor 244, a silicon controlled rectifier (SCR) 246, and a trigger coil 248. The trigger power supply 210 converts the AC power to direct current, e.g., using step-up or step-down transformers, to have a trigger voltage between 100 and 1000 V, and preferably between 100 and 500 V, which is input to the trigger circuit 240. The trigger voltage is used to energize the trigger coil 248 which outputs a voltage pulse between 5,000 to 30,000 V, and preferably between 10,000 and 20,000 V, when the system controller 146 gates the SCR 246 "ON". The voltage pulse is used to ionize the gas in the high intensity light source 250, which lowers the resistance within the high intensity light source 250, to allow the discharging of the stored energy in the capacitor bank(s) 230 through the high intensity light source, e.g., by electrically connecting the anode to the cathode, to flash the high intensity light source. It is appreciated that the system controller 146, when gating the SCR 246 "ON" can inhibit the capacitor charging power supply 205 from charging the capacitor bank 230.

It is appreciated that the system controller 146 controls the charging, discharging, and/or selection of the capacitor bank(s) 230 based on the amount of fluence needed for disinfection/treatment by the high intensity light source for a disinfection rate of up to 99.9999%, e.g., between 4-log and 6-log reduction/inactivation of the virus. While the use of the DMX control is discussed above, it is appreciated that the system controller 146 can include a control algorithm that includes deep learning, machine learning, and/or artificial intelligence systems to control the system 100 and/or the power supply system 170 based on input data received from a sensor, e.g., UV light sensor, a pyroelectric or photodiode sensor, etc., or from a data source, e.g., a computer database, where the input data is received by at least one of the Bluetooth module, Wi-Fi module, or cellular module. It is appreciated that the data source can include a data source of the different contaminants typically found in specific water supplies, on specific surfaces, in specific air supplies, on specific fruits and produce and the amount of fluence (which includes duration) to disinfect the same to up to at least 99%, and preferably up to 99.9%, and most preferably up to 99.9999%, disinfection of biologics and/or contaminants. Thus, based on the input data, the controller 146 can automatically adjust the charging of the capacitor bank(s) based on the input data and/or control the discharge of the capacitor bank(s), e.g., by controlling the IGBT 260, for controlling the amount of fluence from the high intensity light source necessary to disinfect the system.

In an embodiment, the controller 146, based on input data from a sensor or data source, determines the amount of fluence necessary for disinfection and then controls the capacitor charging power supply 205 to supply the necessary voltage to the capacitor bank 230 to provide the energy to the high intensity light source 250 to produce the necessary amount of fluence. The controller 146 using AI or machine learning can produce and adjust the necessary amount of fluence, by controlling at least the amount of voltage supply to the capacitor bank 230, the voltage charged in the capacitor bank 230, the voltage discharged from the capacitor bank 230, the high intensity light source flash time and pulse rates. The controller 146 can also control the light spectrum produced by the high intensity light source, e.g., by controlling the high intensity light source to emit the entire spectrum of 100-1100 nm, or a specific spectrum of 200-400 nm, or a specific UVC wavelength between 220 nm and 280 nm. Thus, in an embodiment, the controller 146 controls the high intensity light source 250 to emit between 30 Joules and 640 Joules of energy per pulse, and preferably over 600 Joules per pulse, for a fluence rate of up to 200 J/cm2, and preferably 10 J/cm$^2$, with a UVC light at a wavelength between 200 and 280 nm for disinfection and treatment. In an embodiment, the controller 146 can receive as input, the energy emitted by the high intensity light source 250, which can be detected using an energy sensor, e.g., a pyroelectric or photodiode sensor, while the light spectrum can be detected using a UV meter. The controller 146 can then adjust the parameters to change the fluence rate, the light spectrum, or the energy output from the high intensity light source 250 to reach the necessary amount of fluence and/or desired light spectrum, e.g., if during one puke, the fluence rate is 2 J/cm$^2$, the subsequent pulse can have a lower fluence rate, if necessary. That is, in an embodiment, the controller 146 allows the power supply to be self-governed by monitoring the output of the high intensity light source and adjusting the same.

Fluence can be defined as the product of fluence rate, exposure time in seconds and total amount of energy incident on the target during the exposure time. It is expressed in J/m$^2$ or J/cm$^2$.

$$F=e*t*f$$

Where F is the fluence (J/cm$^2$), "e" is the energy per pulse J/cm$^2$/pulse, "t" is the time in seconds and "f" is the frequency.

In an embodiment that includes multiple high intensity light sources, the controller 146 is able to adjust sequences, flashing times, and energy input to the multiple high intensity light sources by monitoring the input data from the sensor(s). If certain flashing of specific high intensity light sources are found to be more effective in disinfecting and treating the contaminants, the controller 146 using the machine learning or AI can determine the amount of energy, wavelengths, and which high intensity light sources are flashed to reach an optimal disinfection and treatment of the contaminants, e.g., between a 4-log and 6-log inactivation.

It is appreciated that by strobing/flashing light at a predetermined pulse rate, fluence rate, peak power/energy, frequency, and/or pulse width, etc., the physical, chemical or microbiological contaminants may be eliminated, reduced, degraded, or rendered inert or nullified. That is, embodiments disclosed herein are applicable to air, liquid, food and crops, and/or surface sterilization, disinfection and/or treatment. It will also be appreciated that for air and/or surface sterilization, disinfection and/or treatment, the high intensity light source(s) 250 may serve as the reactor itself (i.e., an enclosure, a shell, and/or a tube, etc. can be optional).

Figure 5:
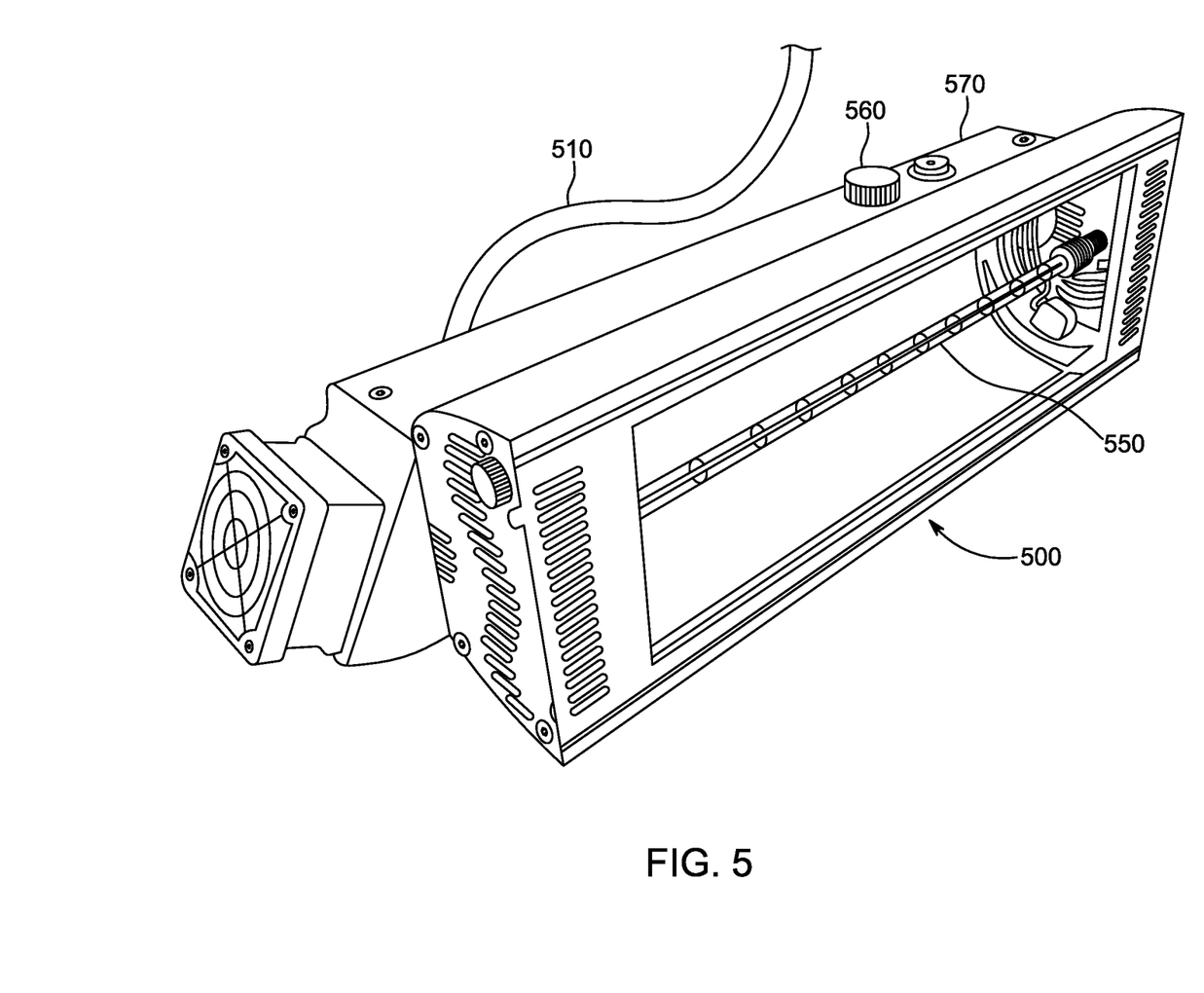
FIG. 5 is a structural schematic diagram of a portable disinfecting device, according to at least one example embodiment described herein.

While the above embodiment is described as part of a liquid treatment system, the power supply as disclosed herein can be applied on any number of different disinfecting devices. FIG. 5 illustrates a power supply that is modified or adapted to a disinfecting device, such as a portable disinfecting device that uses a xenon lamp. In this case, the portable disinfecting device 500 includes a power supply 570 integrated into the control circuitry of the portable disinfecting device 500. The power supply 570 includes the capacitor charging power supply and the trigger power supply and is connected to an external AC power source 510.

The capacitor charging power supply is connected to a capacitor bank via the high voltage output of the capacitor charging power supply, where the capacitor bank (not shown) comprises a plurality of capacitors 232. The capacitors 232 can be pulse type capacitors that are connected in series to increase the voltage rating of the capacitor bank 230 and/or in parallel to increase the capacitance of the capacitor bank 230. The pulse type capacitors have ratings between 1000 and 10,000 uF, and preferably have a rating between 1000 and 5000 uF. The capacitors in the capacitor bank have a diameter between 20 and 60 mm, and preferably between 35-45 mm, and have a length between 40-100 mm, and preferably between 55-80 mm.

The capacitor bank is connected to high intensity light source 550, e.g., a xenon lamp, at the anode to supply the voltage for operating the high intensity light source. It is appreciated that while the voltage needed for the high intensity light source is dependent on the specific model of the high intensity light source, generally, the voltage necessary for operation of the high intensity light source ranges from about 200 volts to 3000 volts, and preferably from about 350 volts to 2000 volts, so that the high intensity light source is able to produce between about 60 Joules to 1000 Joules of energy, and preferably between 60 Joules and 700 Joules, and most preferably over 600 Joule, for a fluence rate of up to 200 J/cm2. In an embodiment, it is appreciated that the voltage can be adjusted by adjusting dial 560 which can be used to control any one of the pulse rate, fluence, peak power/energy, frequency, and/or pulse width, etc., which in turn is used to control the charging of the capacitors in the capacitor bank. The portable disinfecting device 500 can include at least one distance sensor that measures the distance of the high intensity light source of the portable disinfecting device 500 from the surface or item to be disinfected. The controller then controls various variables of the portable disinfecting device, such as flash speed and flash time, to produce the necessary amount of fluence based on the distance between the high intensity light source, the surface or item to be disinfected, and/or the desired wavelengths for disinfection. It is appreciated that a controller can be used for the automatic control of the portable disinfecting device based on surface detection, data input from a data source, distance sensors to determine the amount of fluence necessary for disinfection and control of the charge of the capacitor bank(s). In an embodiment, the portable disinfecting device can include a Bluetooth, Wi-Fi, or cellular module or SSD module for receiving as input data the amount of fluence necessary for treatment of certain foods and/or surfaces from contaminants. The controller can then be used to control the charge supply to the capacitor bank, the charge of the capacitor bank, the discharge of the capacitor bank, and/or the IGBT to produce the necessary fluence rate of the high intensity light source.

In an embodiment, a method for supplying power to a high intensity light source of a treatment and/or disinfection system is provided. The method begins with receiving an input data, for example, from a sensor or data source, and determining a voltage and/or energy necessary for the treatment of contaminant(s) using a high intensity light source. It is appreciated that the amount of voltage and/or energy is adjustable depending on the specifics of the high intensity light source and/or pulsing requirements for treatment/disinfection and can range from about 200 volts to 3000 volts, and preferably from about 350 volts to 2000 volts, to produce about 60 Joules to 1000 Joules of energy per pulse, and preferably between 60 Joules and 700 Joules v, and most preferably between 240 to 640 Joules per pulse for a fluence rate of up to 200 J/cm$^2$ for a single high intensity light source.

A capacitor power supply is used for charging a capacitor bank, where the capacitor bank is connected to the capacitor power supply and the high intensity light source. The capacitor bank includes a plurality of capacitors connected in series and/or in parallel, where the capacitor bank is configured to produce an adjustable voltage and/or energy supply to the high intensity light source. The capacitor bank can then be charged to the desired voltage and/or energy amount necessary for the emission of energy from the high intensity light source, e.g., the fluence rate. The amount of voltage charged and/or discharged from the capacitor bank is able to be varied based on at least the amount of energy supplied from the capacitor power supply, the high intensity light source flash time, the type of high intensity light, pulse rates, and the amount of energy to be supplied to the high intensity light source to produce the necessary fluence rate. In an embodiment, the method can comprise the step of sensing the amount of energy emitted from the high intensity light source, which can range from 30 Joules to 640 Joules of energy per pulse. The energy emitted can be detected using an energy sensor, e.g., a pyroelectric or photodiode sensor.

The capacitor bank includes a plurality of cells, where each cell includes a capacitor, a reverse biased diode to protect the capacitors from reverse voltage during a discharge, and a resistor to assure that the capacitors all charge to the same voltage. The capacitor bank can include at least a two capacitor banks, where one of the capacitor banks is a high voltage capacitor bank for supplying voltages between 800 and 1600 V, and a low voltage capacitor bank for supplying voltages between 350 and 700 V. The method can further include charging the low voltage capacitor bank to a predetermined low voltage and/or charging the high voltage capacitor banks at a predetermined high voltage.

Next, a trigger circuit having a trigger coil connected to the light source is triggered to turn on the high intensity light source. For example, a trigger power supply can be used for the input voltage for trigging on the trigger circuit, where the input voltage is between 100 and 1000 V, and preferably between 100 and 500 V, by gating the SCR "ON". The trigger coil 248 is then used to output a voltage pulse between 5,000 to 30,000 V, and preferably between 10,000 and 20,000 V, to the high intensity light source, which ionizes the gas in the high intensity light source to lower the resistance within the high intensity light source to allow the discharging of the stored energy in the capacitor bank through the high intensity light source, e.g., the ionized gas connects the anode and cathode of the high intensity light source.

It is appreciated that the lamp flash time can be controlled, e.g., shortened, by gating "OFF" an IGBT during the flash. The IGBT is connected in series with the high intensity light source, which allows the adjusting of the flash durations by providing a current path for the voltage supplied to the high intensity light source when the IGBT is gated "OFF". The puke rates can be controlled to range from 100 microseconds to over 20 milliseconds and the energy supplied can be adjusted by changing the pulse rates, e.g., ranging from 0.5 to 2 pulses per second, and cutting off the pukes over various puke rates, e.g., termination after between 0.1-5 ms, and preferably at 0.5 ms, as necessary for the treatment and disinfection of the contaminants. It is appreciated that by strobing/flashing light at a predetermined pulse rate, fluence, peak power/energy, frequency, and/or pulse width, etc., the physical, chemical or microbiological contaminants may be eliminated, reduced, degraded, or rendered inert or nullified.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Different features, variations and multiple different embodiments have been shown and described with various details. What has been described in this application at times in terms of specific embodiments is done for illustrative purposes only and without the intent to limit or suggest that what has been conceived is only one particular embodiment or specific embodiments. It is to be understood that this disclosure is not limited to any single specific embodiments or enumerated variations. Many modifications, variations and other embodiments will come to mind of those skilled in the art, and which are intended to be and are in fact covered by both this disclosure. It is indeed intended that the scope of this disclosure should be determined by a proper legal interpretation and construction of the disclosure, including equivalents, as understood by those of skill in the art relying upon the complete disclosure present at the time of filing.

The herein described subject matter sometimes illustrates different components contained within, or connected with, different other components. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A power supply circuit for a treatment and/or disinfection system using a high intensity broad-spectrum pulsed light comprising:
   at least one capacitor power supply to supply power to a capacitor bank;
   the capacitor bank connected to the at least one capacitor power supply and a high intensity light source, the capacitor bank comprising a plurality of capacitors connected in series and/or in parallel, wherein the capacitor bank is configured to be adjustable to adjust an amount of energy supplied to the high intensity light source;
   a trigger circuit including a trigger coil connected to the high intensity light source for triggering on the high intensity light source; and
   a controller to:
   receive an input data from at least one of a sensor or data source,
   control charging of the capacitor bank to power the high intensity light source at a desired voltage by controlling voltage from the at least one capacitor power supply, and
   trigger the trigger circuit to turn on the high intensity light source at the desired voltage, wherein the desired voltage is based on at least the input data to determine an amount of fluence necessary to treat contaminants using a strobe pulsed light.

2. The circuit according to claim 1, wherein the capacitor bank comprises at least two capacitor banks connected in parallel,
   wherein the controlled charging of the at least two capacitor banks comprises charging at least one of the at least two capacitors banks at a low voltage and/or charging the other of the at least two capacitors banks at a high voltage.

3. The circuit according to claim 2, wherein the low voltage capacitor bank comprises at least two capacitors and is adjustably charged between 350 V and 700 V.

4. The circuit according to claim 2, wherein the high voltage capacitor bank comprises at least six capacitors and is adjustably charged between 800 V and 1,600 V.

5. The circuit according to claim 1, wherein the controller is further configured to stop the at least one power supply from charging the capacitor bank when the trigger circuit is trigged to turn on the high intensity light source.

6. The circuit according to claim 1, wherein the high intensity light source includes a non-mercury flash lamp to generate the pulsed light.

7. The circuit according to claim 1, wherein the plurality of capacitors are pulse-type capacitors that are connected in series and parallel to supply a specific amount of energy to the high intensity light source.

8. The circuit according to claim 1, wherein the high intensity light source is a xenon lamp.

9. The circuit according to claim 1, further comprising:
   an insulated-gate bipolar transistor connected to the high intensity light source, wherein the insulated-gate bipolar transistor provides a current path for the voltage supplied to the high intensity light source.

10. The circuit according to claim 1, further comprising:
    at least one of a solid state storage module, a cellular module, a Wi-Fi module, and a Bluetooth module, wherein at least one of the solid state storage module, the cellular module, the Wi-Fi module and the Bluetooth module is configured to receive the input data from the at least one sensor or data source.

11. The circuit according to claim 1, wherein the trigger circuit comprises a trigger power supply, first resistor, a first capacitor, a silicon controlled rectifier, and a trigger coil,
    wherein the first resistor, the first capacitor, the silicon controlled rectifier, and the trigger coil are configured to produce a high voltage pulse to trigger the high intensity light source on.

12. The circuit according to claim 1, further comprising:
    at least one sensor to sense an energy of the pulsed light.

13. The circuit according to claim 1, wherein the controller is configured to control the power to the high intensity light source to have a repetition rate that is adjustable between 2 pulses per second to 0.5 pulse per second.

14. A treatment and/or disinfection system comprising the circuit according to claim 1 and a high intensity light source.

15. A method for supplying power to a high intensity light source of a treatment and/or disinfection system using a high intensity broad-spectrum pulsed light, the method comprising:

receiving input data from at least one of a sensor or data source, determining a voltage for an amount of fluence necessary for the treatment of contaminants, charging a capacitor bank from at least one capacitor power supply, the capacitor bank being connected to the at least one capacitor power supply and a high intensity light source, the capacitor bank comprising a plurality of capacitors connected in series and/or in parallel, wherein the capacitor bank is configured to be adjustable to adjust an amount of energy supplied to the high intensity light source, wherein charging the capacitor bank comprises charging the capacitor bank to the voltage, triggering a trigger circuit having a trigger coil connected to the high intensity light source to turn on the high intensity light source, and controlling the high intensity light source at the voltage to strobe a pulsed light with the necessary fluence to treat the contaminants.

16. The method according to claim 15, wherein the capacitor bank comprises at least two capacitor banks, wherein charging the capacitor bank further comprises charging at least one of the at least two capacitors banks at a low voltage and/or charging the other of the at least two capacitors banks at a high voltage.

* * * * *